United States Patent [19]
Ali et al.

[11] Patent Number: 4,481,194
[45] Date of Patent: Nov. 6, 1984

[54] DES-PROLINE-DES-GLYCINE VASOPRESSIN ANTAGONISTS

[75] Inventors: Fadia E. Ali, Cherry Hill, N.J.; William F. Huffman, Malvern, Pa.

[73] Assignee: SmithKline Beckman Corporation, Philadelphia, Pa.

[21] Appl. No.: 586,934

[22] Filed: Mar. 7, 1984

[51] Int. Cl.³ .................... A61K 37/00; C07C 103/52
[52] U.S. Cl. .............................. 424/177; 260/112.5 R
[58] Field of Search .................. 424/177; 260/112.5 R

[56] References Cited
U.S. PATENT DOCUMENTS

| | | | |
|---|---|---|---|
| 4,367,225 | 1/1983 | Manning et al. | 424/177 |
| 4,399,125 | 8/1983 | Manning et al. | 424/177 |

*Primary Examiner*—Delbert R. Phillips
*Attorney, Agent, or Firm*—William H. Edgerton; Richard D. Foggio; Alan D. Lourie

[57] ABSTRACT

Certain heptapeptides which have structures characterized by being a six unit cyclic peptide ring with an arginine or lysine tail have vasopressin antagonist activity. An important species of the group is [1-($\beta$-mercapto-$\beta,\beta$-cyclopentamethylenepropionic acid)-2-(O-ethyl-D-tyrosine)-4-valine-7-desproline-8-arginine-9-desglycine]-vasopressin.

16 Claims, No Drawings

DES-PROLINE-DES-GLYCINE VASOPRESSIN ANTAGONISTS

This invention relates to cyclic heptapeptides which have vasopressin antagonist activity. More specifically, these new chemical compounds have structures which are characterized by the lack of both a prolyl unit at position 7 and a glycyl unit at position 9 of the 1-Pmp-VSP antagonist structure.

BACKGROUND OF THE INVENTION

M. Manning, W. H. Sawyer and coworkers have published a series of papers describing various [1-($\beta$-mercapto-$\beta$,$\beta$-cyclopentamethylenepropionic acid)-4-valine]-arginine-vasopressin congeners which have antivasopressin activity. Representative of these are EPA No. 61,356, U.S. Pat. Nos. 4,367,225 and 4,399,125.

All of the Manning compounds have a tripeptide chain attached at unit 6 of the 6-unit dithio ring and are, of course, nonapeptides. The present compounds are distinguished over these by being des-Pro[7] des-Gly[9] vasopressins yet having substantial antagonist activity.

Also, a previously filed U.S. patent application, Ser. No. 467,117 filed Feb. 16, 1983, discloses certain octapeptide vasopressin congeners which have the 9-Gly unit deleted and which have potent VSP antagonist activity.

All of the previously disclosed compounds have structures which have an essential proline-like unit at position 7 of VSP. The compounds of this invention have no such unit in their structures and have substantial VSP antagonist of aquaretic activity.

In the description herein and in the claims, the nomenclature common in the art of peptide and vasopressin chemistry is used. When no configuration is noted, the amino acid unit is in the L, or naturally occuring, form. In certain structural formulas, the thio members of the Pap and Cys units are added for clarity.

Certain of the peptide art designations used herein are the following: Pap, $\beta$-mercapto-$\beta$,$\beta$-cycloalkylenepropionic acid; Pmp, $\beta$-mercapto-$\beta$,$\beta$-cyclopentamethylenepropionic acid; Abu, $\beta$-aminobutyric acid; Chg, cyclohexylglycine; Cha, cyclohexylalanine; Pba, aminophenylbutyric acid, Gln, glutamic acid amide; Gly, glycine; Tyr, tyrosine; Phe, phenylalanine; Val, valine; Ile, isoleucine; Nle, norleucine; Leu, leucine; Ala, alanine; Lys, lysine; Arg, arginine; Asn, asparagine; Tos, tosylate; BHA, benzhydrylamine; DIEA, diisopropylethylamine; 4-MeBzl, 4-methylbenzyl; TFA, trifluoroacetic acid; DCC, dicyclohexylcarbodiimide; HBT, hydroxybenzotriazole; ACM, acetamidomethyl.

DESCRIPTION OF THE INVENTION

The des-Pro-des-Gly-VSP compounds of the invention are illustrated by the following structural formula:

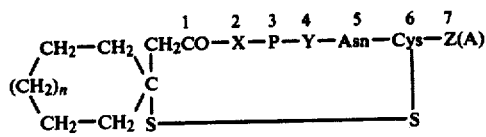

in which:
P is Phe or Phe(4'-Alk);

X is D-Phe, D-Val, D-Nva, D-Leu, D-Ile, D-Pba, D-Nle, D-Cha, D-Abu, D-Met, D-Chg, D or L-Tyr or D or L-Tyr(alk);
Y is Val, Ile, Abu, Ala, Chg, Gln, Lys, Cha, Nle, Phe, Leu or Gly;
Z is D-Arg, L-Arg, D-Lys or L-Lys;
A is OH, NH$_2$ or NHAlk;
n is 0–2, or pharmaceutically acceptable salts, prodrug esters or complexes thereof.

"Alk" in formula 1 and hereafter represents a lower alkyl of 1–4 carbons which is optionally attached either to the nitrogen at A, to the oxygen substituent of the tyrosine unit when the latter is present at position 2 or at the 4'-position of Phe at position 3. Such alkyl substituents include methyl, ethyl, n-propyl, isopropyl or butyl. Preferably Alk is methyl or ethyl. "Bzl" represents benzyl.

When the term, "vasopressin" or "VSP" is used, it means L-arginine vasopressin (AVP) unless otherwise modified to indicate a D-arginine, D-lysine or L-lysine vasopressin. The AVP derivatives of this invention are preferred. In the compounds represented by formula I, those with structures having A as NH$_2$ are also preferred for VSP antagonism.

A subgeneric group of compounds of this invention comprises compounds of formula I in which P is Phe, X is D-Tyr(Et); Y is Val or Abu; n is 1; Z is L-Arg and A is NH$_2$.

Also included in this invention are various derivatives of the compounds of formula I such as addition salts, prodrugs in ester or amide form and complexes. The addition salts may be either salts with pharmaceutically acceptable cations such as NH$_4^\ominus$, Ca$^{++}$, K$^\ominus$ or Na$^\ominus$ at the terminal acid group or with a pharmaceutically acceptable salt at a basic center of the peptide (as in the Arg units). The acetate salt forms are especially useful although hydrochloride, hydrobromide and salts with other strong acids are useful. The compounds, also, form inner salts or zwitter ions as when a terminal carboxy group is present. Prodrugs are simple derivatives of the compounds of formula I which degrade in vivo to give the parent compound. The ester prodrug forms are, for example, lower alkyl esters of the acids of formula I which have from 1–8 carbons in the alkyl radical or aralkyl esters such as various benzyl esters. Other latentiated derivatives of the compounds of formula I will be obvious to those skilled in the art. "Complexes" include various solvates such as hydrates, alcoholates or those with supporting resins, such as a Merrifield resin.

The compounds of formula I are prepared by cyclizing a linear heptapeptide intermediate of this invention by means of the two mercapto groups located, respectively, at the cysteine unit at position 6 and the $\beta$-mercapto-$\beta$,$\beta$-cyclopolyalkylene-propionic acid unit (Pap) at position 1. The cyclization reaction occurs in the presence of a mild oxidizing agent which is capable of oxidizing a mercaptan to a disulfide.

For example, oxidation of the following linear heptapeptide;

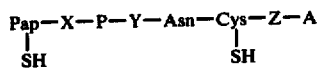

in which P, X, Y, Z, and A are as defined for formula I, with the mercapto groups (—SH) being members of the Pap and Cys units, is carried out as described generally above. For example, an excess of an alkali metal ferricyanide, such as potassium or sodium ferricyanide, is used, with the linear intermediate dissolved in a suitable unreactive solvent, preferably in an aqueous solvent, at a neutral pH, about 7-7.5, at ambient temperature, or lower, until the reaction is substantially complete. Preferably, the concentrations of the linear peptide dimercaptan and the oxidizing agent are low, say 0.01 molar concentration of oxidizing agent in several liters of aqueous solution to cyclize 1-5 grams of dimercaptan. Other solvents may be added especially methanol, ethanol or isopropanol.

Other mild oxidation agents having an oxidation potential roughly equivalent to ferricyanide may also be used for the ring closure reaction. Oxygen, diiodoethane or iodine are alternatives. Of course, one skilled in the art will recognize that certain cyclization methods are not appropriate if an interfering reaction site is present in the structure of the starting material of formula II. The linear mercaptan starting material may or may not have protecting groups common to the art present at the various amino acid units or at the mercapto positions. In the former case, the protecting groups are removed after cyclization. In the case of the ACM-SH protecting groups, removal of the protective group and cyclization are both accomplished using iodine in aqueous methanol. Usually, however, the free linear peptide is cyclized.

The desired cyclic des-proline des-glycine peptide of formula I is conveniently isolated by acidifying the aqueous oxidation mixture, such as using glacial acetic acid, and passing the reaction mixture over an ion-exchange chromatographic column, for example, over a weakly acid, acrylic resin column with acid elution, or by gel filtration over a bead-formed gel prepared by cross-linking dextran with epichlorohydrin.

In an alternative reaction sequence for preparing the compounds of this invention, for example, the intermediate of formula II in which the Arg($NH_2$) unit at position 7 is missing is cyclized as described above and the resulting Cys acid is, then, condensed in a N-protected Arg($NH_2$) derivative, such as a protonated derivative, or Arg($NH_2$) itself. Reaction conditions for the tail unit attachment are those of any amide producing method known to the peptide art but, particularly, reaction of an amino acid or amide ($NH_2$-Z-A) whose carboxylic acid group, if present, is protected, as described below, with the 6-Cys acid in the presence of DCC and HBT is used. The protecting groups which may be present on the cyclic Cys acid or on the tail unit are, then if present, removed to give the products of this invention. Reaction conditions should be selected to minimize racemization of the Cys unit as known to the art.

The important intermediates of formula II, in free or protected form are conveniently prepared using solid-phase methods of peptide synthesis as discussed in M. Manning et al., J. Med. Chem. 25 46 (1982). A commercial benzhydrylamine support resin (BHR) is used to prepare the end products of formula I in which A is $NH_2$ (the amides) and a chloromethyl support resin (CMR) is used to prepare the compounds of formula I in which A is OH (the acids).

The peptide chain of the linear peptides of formula II is built up, stepwise, proceeding from unit 8 working toward unit 1. Each unit is properly protected as known in the peptide art and as described below. The sequence of step reactions is conveniently carried out in a Beckman 990B peptide synthesizer without isolation of each intermediate peptide. The details of the procedure are in the working examples presented hereinafter.

The various amino acids, which are consecutively added to the resin supported chain are protected as known to the art. For example, the Boc protecting group is used for an amino group especially at the α-position; benzylthiomethyl, ethylcarbamoyl, adamantyl, t-butyl, acetamidomethyl, trityl or an optionally substituted benzyl, for the mercapto groups at the Pap and Cys units; nitro; carbobenzoxy, methylene-2-sulfonyl or tosyl for the Arg unit; and ethyloxycarbonyl or an optionally substituted carbobenzoxy (Z) for the Tyr or Lys units. The protective groups should, most conveniently, be those which are easily removed, that is, using acid treatment for the tert.-butyloxycarbonyl (Boc) group, sodium-liquid ammonia or modified catalytic hydrogenation for the benzyl or carbobenzoxy groups.

The protected linear peptide intermediate is split from the carrying resin matrix, for example, by using ammonia in an aqueous miscible solvent, and, then, is treated to remove the protective groups, such as by using sodium-liquid ammonia. This procedure gives the amide derivative of the linear heptapeptide.

More conveniently, the two steps are combined by treating the resin supported peptide with anhydrous hydrogen fluoride (HF) in a suitable organic solvent, such as anisole, to give the des-proline peptide intermediate of formula II in good yield.

The compounds of this invention have potent vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. We believe the mechanism of action is at the vasopressin receptors [$V_2$-receptors] located on the plasma membrane of certain renal epithelial cells. The most notable pharmocodynamic effect of the ADH antagonists of the invention is that of a water diuretic rather than of a natriuretic such as a thiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease.

The second group of vasopressin receptor sites are the vascular pressor sites ($V_1$-receptors) within the cardiovascular system itself. These may also be somewhat antagonized by the compounds of this invention. Dysmenorrhea is another utility for the compounds of this invention when administered intravenously or intranasally.

The compounds of this invention, therefore, are used to treat edema or to expell water in patients in need of such treatment by administering internally, particularly parenterally or by insufflation, a nontoxic but effective quantity of the chosen compound, preferably combined with a pharmaceutical carrier. Dosage units of the active ingredient are selected from the range 0.05 to 20 mg/kg, preferably 1 to 5 mg/kg, based on a 70 kg patient. The dosage units are administered from 1 to 5 times daily.

The pharmaceutical composition which contains an active ingredient of formula I comprises a dosage unit as described above dissolved or suspended in a standard liquid carrier, such as isotonic saline, contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparations, gels, buffers for isotonic preparations, emulsions or aerosols.

Antagonistic activity toward the natural antidiuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopression binding activity are described by F. Stassen et al., J. Pharmacology and Experimental Therapeutics, 223, 50–54 (1982).

In the test procedure for assay of adenylate cyclase activity, the amount of $^{32}P$/cAMP formed in the absence of medullary membrane is determined (blank). The blank value is subtracted from all experimental data. The compound is tested for its effect on basal adenylate cyclase activity and/or on vasopressin stimulated activity. Each determination is carried out in triplicate. The Ka value is derived from a Lineweaver-Burke plot. Rel. $V_{max} = (V_{max} drug/V_{max}$ vasopressin$) \times 100$. $K_i = I/[Ka'/Ka) - 1]$ where I is the concentration of the antagonist, and Ka' and Ka are the concentrations of vasopressin required to give half maximal activity of adenylate cyclase in the presence and absence of antagonist, respectively.

In the test procedure for binding assays, the amount of $^3$H-vasopressin bound in the absence and in the presence of an excess of vasopressin ($7.5 \times 10^{-6}M$) is measured in triplicate. These values represent total and non-specific binding, respectively. The $K_B$ of a compound is derived from the equation for competitive inhibition: $K_B - IC_{50}/(1 + L/K_D)$, where $IC_{50}$ is the concentration required for 50% inhibition of $^3$H-vasopressin ($K_D = 3.6 \times 10^{-9}M$; 1 SD $= 0.4 \times 10^{-9}M$). This is the average $K_D$ value determined on 3 preparations of hog kidney membranes.

The assay for anti-ADH activity is the hydropenic rat protocol is described below:

HYDROPENIC RAT SCREEN

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/kg H$_2$O. A tolerance test is used to determine significance. ED$_{300}$ is defined as the dose of compound ($\mu$g/kg) required to lower urine osmolality to 300 m-Osmoles/kg.

TABLE 1

| Compound | Anti-ADH Activity | | |
|---|---|---|---|
| | In Vivo (Rat) | In Vitro (Pig) | |
| | ED$_{300}$ ($\mu$g/kg)* | Ki (nM) | B$_B$ (uM) |
| A | 74.6* | 2.5 | 9.0 |
| B | 121.8* | 6.2 | 13.0 |
| C | 11.0* | 9.8 | 13.0 |

(A) [1-($\beta$-mercapto-$\beta$,$\beta$-cyclopentamethylenepropionic acid)-2-(O—ethyl-D-tyrosine)-4-valine-7-desproline-8-arginine-9-desglycine]-vasopressin
(B) 1-($\beta$-mercapto-$\beta$,$\beta$-cyclopentamethylenepropionic acid)-2-(O—ethyl-D-tyrosine)-4-$\alpha$-aminobutyric acid-7-desproline-8-arginine-9-desglycine]-vasopressin
(C) [$\beta$-mercapto-$\beta$,$\beta$-cyclopentamethylenepropionic acid)-2-(O—ethyl-D-tyrosine)-4-valine-8-arginine]-vasopressin

*Estimated dose of peptide delivered ip stat ($\mu$g/kg) which results in a reduction of U$_{osm}$ from hydropenic levels to 300 m-Osmoles/kg H$_2$O.

The following examples are intended solely to teach the preparation of the compounds of this invention. All temperatures are in degrees Centigrade.

EXAMPLE 1

Solid Phase Synthesis of Pmp-4(MeBzl)-D-Tyr(Et)-Phe-Y-Asn-Cys(4-MeBzl)-Arg(Tos)-BHA resin:

For the solid phase synthesis of the titled resin-supported peptides, Boc. Arg(Tos)BHA resin (1.34 mmol/g of resin) was used as a starting material. It was prepared by reacting BOC-Arg(Tos), 3 mmol, with the benzhydrylamine resin, 1.0 mmol, in dimethylformamide for two hours. The benzhydrylamine resin as a free base was swelled in methylene chloride overnight. It was washed once with 7% diisopropylethylamine (DIEA) in methylene chloride, then 6×1 min. with methylene chloride, and finally 2×1 min. with predried dimethylformamide. The loading of BOC-Arg-(Tos) on the resin was carried out twice on the shaker using 1-hydroxybenzotriazole (HBT, 6 mmol), and dicyclohexylcarbodiimide (DCC, 3 mmol). A quantitative ninhydrin test and amino acid analysis were performed routinely after loading to determine the percentage loading on the resin. Loading in this particular run was 53%, i.e., only 0.709 mmol/g of resin was available.

The appropriately protected amino acids were coupled sequentially on the Boc. Arg(Tos)-resin using the Beckman peptide synthesizer 990-B. The program used for each coupling, except Boc-Asn and Pmp(4-MeBzl), was as follows:

(1) Washed with methylene chloride (3 times, 1 min).
(2) Prewashed with 50% trifluoroacetic acid in methylene chloride (1 time, 1 min).
(3) Deprotection with 50% trifluoroacetic acid in methylene chloride (30 min).
(4) Washed with methylene chloride (3 times, 1 min).
(5) Prewashed with 7% DIEA in methylene chloride (1 time, 1 min).
(6) Neutralized with 7% DIEA in methylene chloride (1 time, 10 min).
(7) Washed with methylene chloride (3 times, 1 min).
(8) Protected amino acid (3 mmol) in methylene chloride, followed by addition of DCC, 3 mmol, 10 ml of 0.3M in methylene chloride, and coupling for two hours.
(9) Washing with methylene chloride (3 times, 1 min).
(10) Washing with ethanol/methylene chloride (1:1) (3 times, 1 min).
(11) Washing with methylene chloride (3 times, 1 min).

In case of coupling of Asn moiety, 1-hydroxybenzotriazole (HBT, 6 mmol) was used, 10 ml of 0.6M in dimethylformamide. Dry dimethylformamide was also used as solvent when Pmp(4-MeBzl) was coupled onto the peptide resin, using 4-dimethylaminopyridine (DAP, 3 mmol). Completion of each coupling reaction was monitored by the ninhydrin test. The p-methylbenzyl group was used to protect the thiol groups of Cys and the pentamethylenemercaptopropionic acid (Pmp) moieties.

After coupling to the Asn amino acid, the resin-supported peptide was split into two halves, 0.355 mmol each, to incorporate separately Boc-Abu or Boc-Val at position 4, and the sequence was continued to Pmp (4-MeBzl) as indicated. The resulting protected peptide resin intermediates, i.e., [Pmp(4-MeBzl)-D-Tyr(Et)-Phe-Y-Asn. Cys(4-MeBzl)-Arg(Tos)-BHA, resin] where Y=Abu or Val, were washed separately with methylene chloride and dried in vacuo overnight to give 0.87 g (Y=Abu), 0.67 g (Y=Val). The latter resin was used for Example 2.

Preparation of
Pmp-D-Tyr(Et)-Phe-Abu-Asn-Cys-Arg(NH$_2$)

Pmp(4-MeBzl)-D-Tyr(Et)-Phe-Abu-Asn-Cys(4-MeBzl)-Arg(Tos)-BHA-resin, 0.87 g in 2 ml of anisole, was reacted with anhydrous hydrogen fluoride (20 ml) at 0° for 50 min. After evaporation in vacuo to dryness, the residue was treated with anhydrous ether, and the crude peptide was extracted with dimethylformamide (50 ml) and 33% acetic acid (60-70 ml) into a 2 liter water. The water-diluted dimercapto heptapeptide was cyclized using 0.01M potassium ferricyanide solution at pH 7.2 until color persisted for 30 min (~30 ml). After the completion of the oxidation reaction, the pH of the solution was adjusted to pH 4.5 by adding glacial acetic acid. This solution was passed through a weakly acid acrylic resin (Bio-Rex 70) column (2.5×12 cm) slowly. The column was eluted with pyridine-acetate buffer (pyridine/glacial acetic acid/water, 30:4:66). The pyridine-acetate solution was removed by distillation in vacuo and the residue was lyophilized from 10% acetic acid to give 115 mg (33%) of crude titled peptide.

Purification of
Pmp-D-Tyr(Et)-Phe-Abu-Asn-Cys-Arg(NH$_2$)

(1) Partition Column, Sephadex, G-25: sample: 115 mg, n-butanol/acetic acid/water, (4:1:5), 72.6 mg
(2) Gel Filtration, G-15, 0.2M acetic acid: 60.5 mg
(3) Preparative HPLC sample: 35.0 mg (from 2), Altex ODS, 10 mm×25 cm 5μ, flow rate 4 ml/min., water/acetonitrile/trifluoroacetic acid (60:40:0.25%), isocratic, 229 nm (2.0 AUFS), injection 4.14 mg) 500 μl. 28 mg pure sample of the titled product.

Physical Data:
Molecular Formula: C$_{45}$H$_{65}$N$_{11}$O$_9$S$_2$.
Molecular Weight: 967.48.
Amino Acid Analysis: Asp (1.00), Abu+Cys (1.35), Tyr (0.74), Phe (0.93), Arg (0.82).
Peptide Content: 65.6%.

| Chromatography Data: | solvent | RF |
|---|---|---|
| Thin layer chromatography (TLC) | Butanol: Acetic Acid/Water/Ethyl acetate (1:1:1:1) | 0.63 |
| | Butanol/Acetic Acid/Water (4:1:5) (Upper) | 0.51 |
| High pressure liquid chromatography (HPLC) isocratic, 0.05 M potassium/ | C-18 column | k' |
| | C-18 column | 4.7 |
| dihydrogen phosphate/acetonitrile (60:40) | | |
| Gradient, 0.05 potassium dihydrogen phosphate/acetonitrile (80:20 to 50:50) | | 15.2 |
| Fast Atom Bombardment "FAB" : | (M + H)$^+$ at 968 (M − H)$^-$ at 966 | |

EXAMPLE 2

Preparation of
Pmp-D-Tyr(Et)-Phe-Val-Asn-Cys-Arg(NH$_2$)

Pmp(4-MeBzl)-D-Tyr(Et)-Phe-Val-Asn-Cys(4-MeBzl)-Arg(Tos)-BHA-resin, 0.67 g from Example 1 in 2 ml of anisole, were reacted with anhydrous hydrogen fluoride (20 ml), at 0° for 50 min. It was worked up as in the previous example, to give 80 mg (23%) of crude titled peptide.

Purification of
Pmp-D-Tyr(Et)-Phe-Val-Asn-Cys-Arg(NH$_2$)

(1) Partition column, Sephadex, G-25: sample: 80 mg, n-butanol/acetic acid/water (4:1:5), 75.7 mg.
(2) Preparative HPLC: sample: 42.7 mg (from 1), Altex ODS, 10 mm×25 cm, 5μ, flow rate 4 ml/min, water/acetonitrile/trifluoroacetic acid (60:40:0.25%), isocratic, 229 nm (2.0 AUFS), injection 4.7 mg/500 μl, 36.8 mg pure titled sample.

Physical Data:
Molecular Formula: C$_{46}$H$_{67}$N$_{11}$O$_9$S$_2$.
Molecular Weight: 981.44.
Amino Acid Analysis: Asp(1.06), Cys(0.37), Val(1.00), Tyr(0.65), Phe(0.91), Arg(1.00).
Peptide content: 87.55%.

| Chromatography Data: | solvent | RF |
|---|---|---|
| Thin layer chromatography (TLC) | n-Butanol/acetic acid/water/ethyl acetate (1:1:1:1) | 0.6 |
| | n-Butanol/acetic acid/water (4:1:5) (Upper) | 0.516 |
| High pressure liquid chromatography (HPLC) isocratic, 0.05 potassium dihydrogen phosphate/acetonitrile (60:40) | C-18 column | K' |
| | | 6.25 |
| Gradient, 0.05 potassium dihydrogen phosphate/acetonitrile (80:20 to 50:50) | | 16.0 |
| Fast Atom Bombardment "FAB": | (M + H)$^+$ at 982 (M − H)$^-$ at 980 | |

EXAMPLE 3

Preparation of
Pmp-D-Tyr-Phe-Val-Asn-Cys-Arg(NH$_2$)

Pmp(4-MeBzl)-D-Tyr(Br-Z)-Phe-Val-Asn-Cys(4-MeBzl)-Arg(Tos)-Resin (4.0 g, prepared by the method from Example 1, in 4.5 ml distilled anisole, is treated with anhydrous hydrogen fluoride (40 ml) at 0° for one hour. After evaporation in vacuo to dryness, the residue is treated with anhydrous ether and extracted to give 1.30 g of crude peptide. The resulting unprotected heptapeptide is cyclized using 0.01M potassium ferricyanide solution at pH 7–7.5 until color persisted for 30 minutes again as described above. The titled compound is isolated and purified as described above.

EXAMPLE 4

Preparation of
Pmp-D-Tyr(Et)-Phe-Val-Asn-Cys-Arg(NHC$_3$H$_7$)

A mixture of 0.1 mmole of (Pmp$^1$-D-Tyr(Et)$^2$-Val$^4$-desPro$^7$desGly$^9$)AVP, prepared as described above, and 0.1 mmole of n-propylamine in 20 ml of dimethylformamide is reacted with 23 mg (0.11 mmole) of DCC and 14 mg (0.11 mmole) of HBT at room temperature for 2 hours. The volatiles are evaporated to give a product residue. The product is purified using (1) gel filtration over G-10-Sephadex eluted with 0.2N acetic acid, (2) high pressure liquid chromatography using 0.05% trifluoroacetic acid in 39% acetonitrile in water and, again, (3) gel filtration to give the pure peptide of the title.

EXAMPLE 5

Substituting a stoichiometric quantity of Boc-L-Tyr(Et) at the 2 unit of the peptide synthesis of Example 1 gives Pmp-L-Tyr(Et)-Phe-Val-Asn-Cys-Arg(NH$_2$).

Substituting in Example 1, using CMR, D-Arg(Tos) at the 7 unit gives Pmp-D-Tyr(Et)-Phe-Val-Asn-Cys-D-Arg(OH).

Substituting Boc-L-Phe(4-Me) for the amino acid at the 3 unit and Boc-Nle at the 4 unit in the synthesizer sequence reactions of Example 1 gives Pmp-D-Tyr(Et)-Phe(4-Me)-Nle-Asn-Cys-Arg(NH$_2$).

Substituting Boc-Nvl for the amino acid at the 4-unit of Example 1 gives Pmp-D-Tyr(Et)-Phe-Nvl-Asn-Cys-Arg(NH$_2$).

Substituting Boc-Cha at the 4 unit gives Pmp-D-Tyr-(Et)-Phe-Cha-Asn-Cys-Arg(NH$_2$).

Substituting Boc-D-Pba at the 2 unit and Boc-Chg at the 4 unit of detailed reaction sequence of Example 1 gives Pmp-D-Pba-Phe-Chg-Asn-Cys-Arg(NH$_2$).

Substituting in Example 1, using CMR, L-Lys(Boc) at the 7 unit, as described in the specification, gives Pmp-D-Tyr(Et)-Phe-Val-Asn-Cys-L-Lys(OH).

Substituting β-(S-benzylmercapto-β-β-cyclotetramethylene)propionic acid (Tmp) for Pmp in Example 1 gives the Tmp$^1$-D-Tyr-(Et)$^2$ derivative of Example 1.

EXAMPLE 6

Parenteral Dosage Unit Compositions

A preparation which contains 0.5 mg of the cyclic octapeptide of Example 2 as a sterile dry powder for parenteral injection is prepared as follows: 0.5 mg of peptide amide is dissolved in 1 ml of an aqueous solution of 20 mg of mannitol. The solution is filtered under sterile conditions into a 2 ml ampoule and lyophylized. The powder is reconstituted before either intramuscular or intravenous injection to a subject suffering from edema susceptible to anti-ADH mechanism of action. The injection is repeated as necessary, from 1–5 times daily or in continuous i.v. drug injection. Other octapeptides of this invention are made up and used in like manner.

Nasal Dosage Unit Compositions 340 mg of finely ground octapeptide of this invention such as the product of Example 2 is suspended in a mixture of 75 mg of benzyl alcohol and 1.395 g of a suspending agent such as a commercial mixture of semisynthetic glycerides of higher fatty acids. The suspension is placed in an aerosol 10 ml container which is closed with a metering valve and charged with aerosol propellants. The contents comprise 100 unit doses which are administered intranasally to an edematous subject from 1–6 times a day.

What is claimed is:

1. A polypeptide having the formula:

$$\begin{array}{c}CH_2-CH_2\ \ CH_2CO-X-P-Y-Asn-Cys-Z(A)\\ /\quad\ \ \ \backslash\ |\qquad\qquad\qquad\qquad\qquad\qquad|\\ (CH_2)_n\qquad\ C\qquad\qquad\qquad\qquad\qquad\qquad|\\ \backslash\qquad\ \ /\,|\qquad\qquad\qquad\qquad\qquad\qquad|\\ CH_2-CH_2\ \ S\text{------------------------}S\end{array}$$

in which:

P is Phe or Phe(4'-Alk);
X is D-Phe, D-Val, D-Nva, D-Leu, D-Ile, D-Pba, D-Nle, D-Cha, D-Abu, D-Met, D-Chg, D or L-Tyr or D or L-Tyr(alk);
Y is Val, Ile, Abu, Ala, Chg, Gln, Lys, Cha, Nle, Phe, Leu or Gly;
Z is D-Arg, L-Arg, D-Lys or L-Lys;
A is OH, NH$_2$ or NHAlk; and
n is 0–2, or a pharmaceutically acceptable salt, prodrug ester or complex thereof.

2. The compound of claim 1 in which Z(A) is Arg(NH$_2$).

3. The compound of claim 1 in which X is D-Tyr-(alk), n is 1 and Z is Arg and A is NH$_2$.

4. The compound of claim 1 having the formula:

$$\begin{array}{c}CH_2-CH_2\ \ CH_2CO-D\text{-}Tyr(Et)\text{-}Phe\text{-}Val\text{-}Asn\text{-}Cys\text{-}Arg(NH_2)\\ /\quad\ \ \ \backslash\ |\qquad\qquad\qquad\qquad\qquad\qquad\qquad\qquad\quad|\\ CH_2\qquad\ \ C\qquad\qquad\qquad\qquad\qquad\qquad\qquad\qquad\quad|\\ \backslash\qquad\ /\,|\qquad\qquad\qquad\qquad\qquad\qquad\qquad\qquad\quad|\\ CH_2-CH_2\ \ S\text{------------------------}S.\end{array}$$

5. The compound of claim 1 having the formula:

$$\begin{array}{c}CH_2\text{-}CH_2\ CH_2CO-D\text{-}Tyr(Et)-Phe-Abu-Asn-Cys-Arg(NH_2).\\ /\quad\ \ \ \backslash\ |\qquad\qquad\qquad\qquad\qquad\qquad\qquad\qquad\quad|\\ CH_2\qquad\ \ C\qquad\qquad\qquad\qquad\qquad\qquad\qquad\qquad\quad|\\ \backslash\qquad\ /\,|\qquad\qquad\qquad\qquad\qquad\qquad\qquad\qquad\quad|\\ CH_2\text{-}CH_2S\text{------------------------}S\end{array}$$

6. A pharmaceutical composition comprising a pharmaceutical carrier and, dispersed therein, a water diuretically effective but nontoxic quantity of a compound of claim 1.

7. The composition of claim 6 in which the compound has the formula:

$$\begin{array}{c}CH_2-CH_2\ \ CH_2CO-D\text{-}Tyr(Et)\text{-}Phe\text{-}Val\text{-}Asn\text{-}Cys\text{-}Arg(NH_2)\\ /\quad\ \ \ \backslash\ |\qquad\qquad\qquad\qquad\qquad\qquad\qquad\qquad\quad|\\ CH_2\qquad\ \ C\qquad\qquad\qquad\qquad\qquad\qquad\qquad\qquad\quad|\\ \backslash\qquad\ /\,|\qquad\qquad\qquad\qquad\qquad\qquad\qquad\qquad\quad|\\ CH_2-CH_2\ \ S\text{------------------------}S.\end{array}$$

8. The composition of claim 6 in which the compound has the formula:

$$\begin{array}{c}CH_2\text{-}CH_2\ CH_2CO-D\text{-}Tyr(ET)-Phe-Abu-Asn-Cys-Arg(NH_2).\\ /\quad\ \ \ \backslash\ |\qquad\qquad\qquad\qquad\qquad\qquad\qquad\qquad\quad|\\ CH_2\qquad\ \ C\qquad\qquad\qquad\qquad\qquad\qquad\qquad\qquad\quad|\\ \backslash\qquad\ /\,|\qquad\qquad\qquad\qquad\qquad\qquad\qquad\qquad\quad|\\ CH_2\text{-}CH_2S\text{------------------------}S\end{array}$$

9. The composition of claim 6 in which the quantity of compound is selected from the range of 0.01–10 mg/kg.

10. The method of inducing a VSP antagonist effect in a patient in need of such an effect comprising administering internally to said patient a nontoxic, effective quantity therefor of a compound of claim 1.

11. The method of claim 10 in which the compound has the formula:

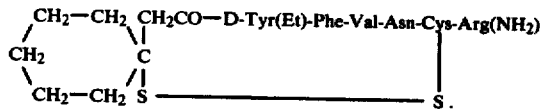

12. The method of claim 10 in which the compound has the formula:

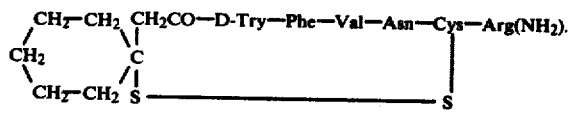

13. The method of claim 10 in which the quantity is selected from the range of 0.01–10 mg/kg which is administered from 1–5 times daily.

14. A polypeptide of the formula:

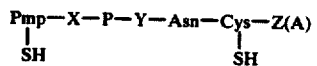

in which:
P is Phe or Phe(4'-Alk);
X is D-Phe, D-Val, D-Nva, D-Leu, D-Ile, D-Pba, D-Nle, D-Cha, D-Abu, D-Met, D-Chg, D or L-Tyr or D or L-Tyr(Alk);
Y is Val, Ile, Abu, Ala, Chg, Gln, Lys, Cha, Nle, Phe, Leu or Gly;
Z is D-Arg, L-Arg, D-Lys or L-Lys; and
A is OH, NH₂ or NHAlK.

15. The compound of claim 14 being Pmp-D-Tyr(Et)-Phe-Val-Asn-Cys-Arg(NH₂).

16. The compound of claim 14 being Pmp-D-Tyr(Et)-Phe-Abu-Asn-Cys-Arg(NH₂).

* * * * *

UNITED STATES PATENT AND TRADEMARK OFFICE
CERTIFICATE OF CORRECTION

PATENT NO. : 4,481,194
DATED : November 6, 1984
INVENTOR(S) : Fadia E. Ali and William F. Huffman It is certified that error appears in the above-identified patent and that said Letters Patent are hereby corrected as shown below:

Column 1, line 44, "β-aminobutyric acid" should read -- α-aminobutyric acid --.

Column 2, lines 33 and 34, "$NH_4 \oplus$ ,Ca ++, , $K \ominus$ or $Na \ominus$" should read: -- $NH_4 \oplus$ ,Ca $\oplus\oplus$ , $K \oplus$ or $Na \oplus$ --.

Column 10, line 60, "-D-Tyr(ET)-" should read -D-Tyr(Et)-.

Column 11, line 19, "-D-Try-" should read -D-Tyr-.

Signed and Sealed this

Sixteenth Day of April 1985

[SEAL]

Attest:

DONALD J. QUIGG

*Attesting Officer*     *Acting Commissioner of Patents and Trademarks*